US00PP12446P2

(12) United States Plant Patent
Hanes

(10) Patent No.: US PP12,446 P2
(45) Date of Patent: Mar. 12, 2002

(54) GERANIUM PLANT NAMED 'FREE DARK RED'

(75) Inventor: Mitchell Eugene Hanes, Morgan Hill, CA (US)

(73) Assignee: Goldsmith Plants Inc., Gilroy, CA (US)

( * ) Notice: Subject to any disclaimer, the term of this patent is extended or adjusted under 35 U.S.C. 154(b) by 0 days.

(21) Appl. No.: 09/335,185

(22) Filed: Jun. 17, 1999

(51) Int. Cl.[7] ..... A01H 5/00
(52) U.S. Cl. ..... Plt./332
(58) Field of Search ..... Plt./332, 324

(56) References Cited

U.S. PATENT DOCUMENTS

PP10,365 P * 4/1998 Utecht ..... Plt./332
PP10,502 P * 7/1998 Lemon ..... Plt./332
PP10,851 P * 4/1999 Utecht ..... Plt./332

OTHER PUBLICATIONS

GTITM UPOVROM Citation for 'Free Dark Red' as per QZ PBR 970753; Jun. 27, 1997.*

* cited by examiner

*Primary Examiner*—Bruce L. Campell
*Assistant Examiner*—Kent L. Bell
(74) *Attorney, Agent, or Firm*—Rothwell, Figg, Ernst & Manbeck

(57) ABSTRACT

A new and distinct ivy geranium plant named 'Free Dark Red' is provided. 'Free Dark Red' is characterized by its green foliage with dark red colored double flowers on large umbels, its fast rooting and vigorous growth.

1 Drawing Sheet

BACKGROUND OF THE NEW PLANT

The present invention comprises a new and distinct ivy geranium plant, botanically known as *Pelargonium peltatum* Bailey, and hereinafter referred to by the name of 'Free Dark Red'.

This new geranium originated from a cross made by the inventor of the seed parent 5651-2 (unpatented), a plant from the breeding line 5651, and the pollen parent 5146-1 (unpatented), a plant from the breeding line 5146. The breeding line 5651 has the commercial variety 'Shiva' (unpatented) as it's pollen parent. The breeding line 5146 has the commercial variety 'Romy' (unpatented) as it's pollen parent.

'Free Dark Red' is the product of a planned breeding program intended to create new geranium plants with red colored flowers, semi-double flower form, and superior cutting productivity.

'Free Dark Red' was created in 1996 in Gilroy, Calif., and has been repeatedly asexually reproduced by cuttings in Gilroy, Calif., and Guatemala over a three year period.

The plant has also been trialed at Okemos, Mich. The plant has been found to retain its distinctive characteristics through successive propagations; and this novelty appears to be firmly fixed and reproduces true to the type.

DESCRIPTION OF THE DRAWING

This new geranium plant is illustrated by the accompanying photographic drawing which shows blooms, buds, and foliage of the plant in full color, the colors shown being as true as can be reasonably obtained by conventional photographic procedures.

DESCRIPTION OF THE NEW CULTIVAR

Figure 1:
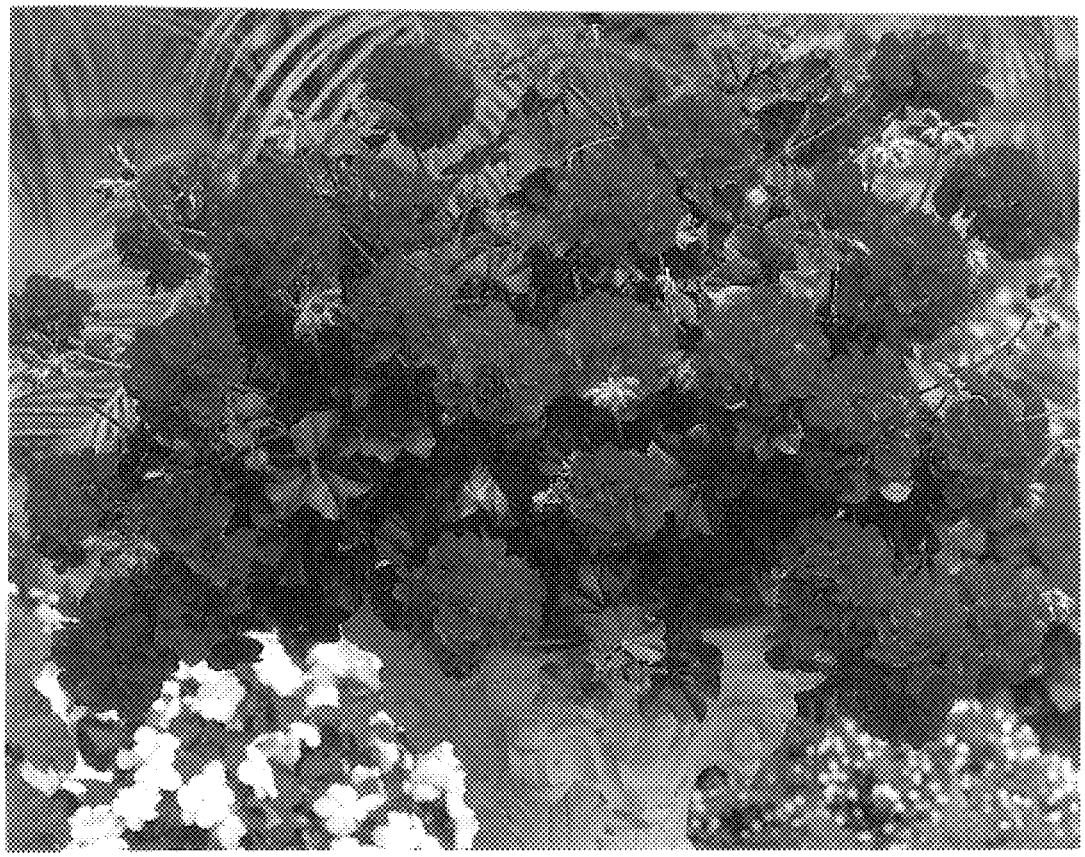
FIG. 1 shows the overall plant habit.

The following detailed descriptions set forth the distinctive characteristics of 'Free Dark Red'. The data for these characteristics were collected from asexual reproductions carried out in Gilroy, Calif. The plant history was taken on 11 week old plants, blossomed under natural light in a greenhouse and color readings were taken in the greenhouse in Gilroy, Calif., under ambient light. Color references are primarily to The R.H.S. Colour Chart of The Royal Horticultural Society of London (R.H.S.).

The Plant

Classification:
*Botanical.*—*Pelargonium peltatum.*
*Commercial.*—Ivy geranium.
Form: Upright spreading.
Height: 24–29 cm., in a 4½ inch pot plant, excluding blooms; plant height from soil level to top of umbels is 29–34 cm; width is 24–34 cm.
Growth: Vigorous, good basal branching, withstands multiple harvests of cuttings, produces a commercially acceptable size flowering plant in a 4 inch pot within 12 weeks and produces a strong, weather resistant plant in outdoor field trials in several different climate zones.
Foliage: Abundant quantity.
Time to produce a finished flowering plant: 12 weeks.

The Leaves

Size: Diameter approximately 6 cm; Length is 3.7–4.8 cm; Apex is acute; Base is cordate.
Shape: Reniform, partly overlapping.
Margin: Entire.
Texture: Leathery and pubescent on both surfaces, especially along veins.

Ribs and veins: Distinctly palmate, 3.4 to 4.5 cm. long.

Color:

*Upper side.*—Green, 137B RHS, with a light zone approximately 1.0–1.5 cm grey-purple RHS 187A.

*Under side.*—Lighter green color, 137C RHS.

Petioles: Approximately 4.5 to 5.5 cm in length; 2–3 mm in diameter and colored yellow-green RHS 144A.

Lateral branches: Length is 23 cm; Internode is 4–6 cm; Color is yellow-green RHS 144A.

Roots: Time to initiate roots is 7–10 days; time to develop roots is 3–4 weeks; description is fibrous, white, slightly hairy.

The Bud

Size:

*Diameter.*—Approximately 7 mm.

*Length.*—Approximately 1.3 cm. at time of bud opening.

Shape: Pointed ovoid.

Color: Petals when sepals first divide, red 46B RHS.

Sepals: 5 in number, flat behind petals. Pointed linear lanceolate, upper and lower color is green, 146C RHS, in an open flower. Length is 1.0–1.2 cm; Width is 4 mm; Apex is cuspidate; Base is truncate.

The Flower

Flowering season: Continuous throughout the year.

Size: Approximately 5.1 cm. diameter, 1.0 cm. deep, irregularly radially symmetrical.

Form: Full double flower.

Petals/petaloids: Approximately 13–15 petals and 3–5 petaloids spatulate shaped. Petals are 3 cm in length and 2 cm in width and petaloids are 1.6–2.2 cm in length and 1 cm in width, obtuse apex, attenuate base and entire, undulated margins. Both petals and petaloids have an upper surface color of both red, RHS 46A and RHS 46B and lower surface of petals and petaloids is red RHS 46A with flecks and striations of RHS 47D. Petals and petaloids soft and satiny.

Pedicel: Approximately 2.0 cm. in length; yellow-green RHS 144A.

Persistence: An open flower will hold its petals until the flower begins to dehisce, or approximately 7–10 days.

Inflorescence

Type: An umbel composed of approximately 15 flowers, erect or laterally ascending; diameter is 9–10 cm; depth is 4.8–5.4 cm from bottom of pedicel to top of umbel.

Peduncle: Approximately 15 cm. in length yellow-green RHS 144A in color.

Reproductive Organs

Stamens:

*Anthers.*—Approximately 7 anthers positioned above the mature stigma, purple, RHS 71A, prior to anthesis.

*Filaments.*—White near base and mid length, graduating to red purple, RHS 67A, near anther.

*Pollen.*—Moderate amount, Orange, RHS 31A, in color.

Pistil:

*Number.*—1.

*Length.*—Approximately 11 mm.

*Stigma.*—4–6 linear lobes of near equal length, curling back toward ovary, purplish-red RHS 59A.

*Style.*—Length: Approximately 6 mm., color: white 156C.

*Ovaries.*—At anthesis, densely pubescent with white hairs, oblong. Green drying to a light brown at maturity.

Fruit/seeds: Occasional seed set; maximum of five seeds per seed spike; seed length is approximately 4 mm; width is 1 mm; color is grey-orange RHS 177B but may darken with age.

Disease/Insect Resistance

No known susceptibility or resistance to typical diseases and insects of geraniums.

Comparison with Parental Cultivars

Parental cultivar 5651-2 is not as branched as 'Free Dark Red'. Also 'Free Dark Red' is a full double flower as compared to single flowers for 5651-2. Parental cultivar 5146-1 also is not as branched as 'Free Dark Red' and has a susceptibility to oedema.

I claim:

1. A new and distinct ivy geranium plant substantially as herein shown and described, named 'Free Dark Red', that is characterized by its green foliage with dark red colored double flowers on large umbels, its fast rooting and vigorous growth.

* * * * *